(12) United States Patent
Amano

(10) Patent No.: US 8,995,477 B2
(45) Date of Patent: Mar. 31, 2015

(54) ULTRASHORT PULSE LASER PROCESSING APPARATUS

(75) Inventor: Masanori Amano, Aichi (JP)

(73) Assignee: Nidek Co., Ltd., Aichi-ken (JP)

( * ) Notice: Subject to any disclaimer, the term of this patent is extended or adjusted under 35 U.S.C. 154(b) by 0 days.

(21) Appl. No.: 13/410,343

(22) Filed: Mar. 2, 2012

(65) Prior Publication Data

US 2012/0224596 A1 Sep. 6, 2012

(30) Foreign Application Priority Data

Mar. 2, 2011 (JP) ................................. 2011-045249

(51) Int. Cl.
| | |
|---|---|
| *H01S 3/067* | (2006.01) |
| *A61F 9/008* | (2006.01) |
| *H01S 3/00* | (2006.01) |
| *H01S 3/23* | (2006.01) |

(52) U.S. Cl.
CPC ............. *A61F 9/0084* (2013.01); *H01S 3/0057* (2013.01); *H01S 3/06754* (2013.01); *H01S 3/005* (2013.01); *H01S 3/2308* (2013.01)
USPC .................... 372/6; 372/25; 372/30; 372/102

(58) Field of Classification Search
USPC ............................................................ 372/6
See application file for complete search history.

(56) References Cited

U.S. PATENT DOCUMENTS

| | | | | |
|---|---|---|---|---|
| 6,249,630 | B1 * | 6/2001 | Stock et al. .................... | 385/123 |
| 6,385,215 | B1 * | 5/2002 | Sumiyoshi ........................ | 372/6 |
| 7,787,175 | B1 | 8/2010 | Brennan, III et al. | |
| 2004/0240037 | A1 | 12/2004 | Harter | |
| 2004/0243112 | A1 | 12/2004 | Bendett et al. | |
| 2005/0041702 | A1 * | 2/2005 | Fermann et al. ................. | 372/25 |
| 2005/0169324 | A1 | 8/2005 | Ilday et al. | |
| 2005/0238070 | A1 | 10/2005 | Imeshev et al. | |
| 2005/0281506 | A1 * | 12/2005 | Okazaki et al. ................. | 385/31 |
| 2006/0291521 | A1 | 12/2006 | Ilday et al. | |
| 2007/0064304 | A1 | 3/2007 | Brennan, III et al. | |
| 2008/0130099 | A1 | 6/2008 | Harter | |
| 2008/0212623 | A1 * | 9/2008 | Bischoff et al. ................. | 372/24 |
| 2009/0097520 | A1 | 4/2009 | Harter | |
| 2010/0130968 | A1 | 5/2010 | Vogler | |
| 2012/0062983 | A1 | 3/2012 | Imeshev et al. | |

FOREIGN PATENT DOCUMENTS

| | | |
|---|---|---|
| JP | 2006007279 | 1/2006 |
| JP | 2006088199 | 4/2006 |

(Continued)

OTHER PUBLICATIONS

Femtosecond Fiber Laser for Micromachining; Uehara Yuzuru, et al.; Apr. 27, 2007.
Communication issued Jun. 18, 2012 by the European Patent Office in counterpart European Application No. 12001403.0.
Office Action dated Dec. 4, 2013, issued by the European Patent Office in counterpart European Application No. 12001403.0.

(Continued)

*Primary Examiner* — Xinning Niu
(74) *Attorney, Agent, or Firm* — Sughrue Mion, PLLC

(57) ABSTRACT

An ultrashort pulse laser processing apparatus for processing a processing target includes: a laser head which includes a seed laser source emitting an ultrashort pulse seed laser, and emits a laser pulse; an optical fiber which guides the laser pulse emitted from the laser head; and an emission end unit which includes a compressor that compresses the laser pulse emitted from the optical fiber to a laser pulse of a predetermined high peak power and emits the laser pulse compressed by the compressor to the target.

5 Claims, 4 Drawing Sheets

(56) References Cited

FOREIGN PATENT DOCUMENTS

| | | |
|---|---|---|
| JP | 2007527732 | 10/2007 |
| WO | 2010-105637 A1 | 9/2010 |

OTHER PUBLICATIONS

Office Action date Jan. 6, 2015, issued by the Japanese Patent Office in counterpart Japanese application No. 2011-045249.

* cited by examiner

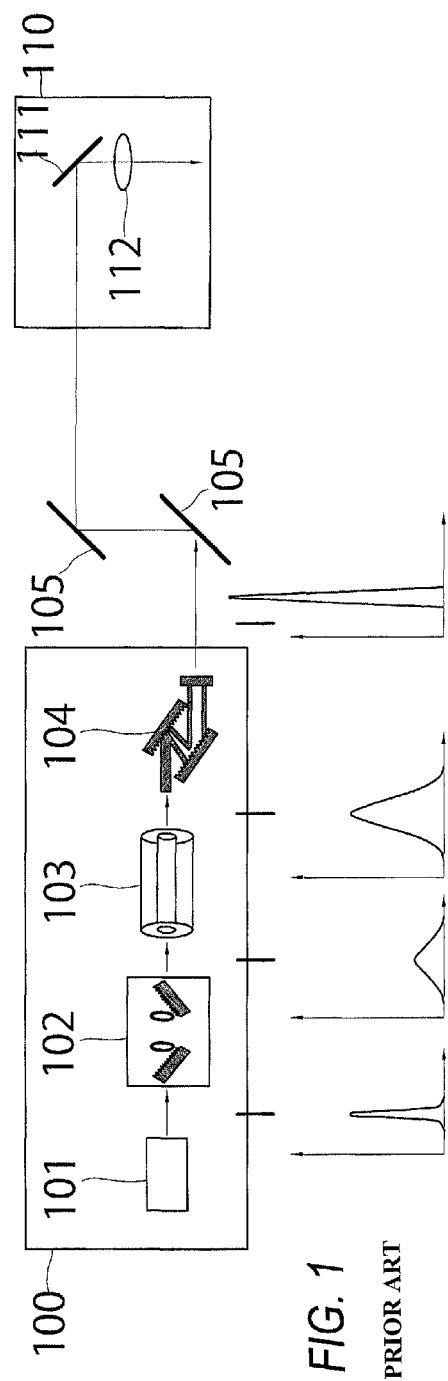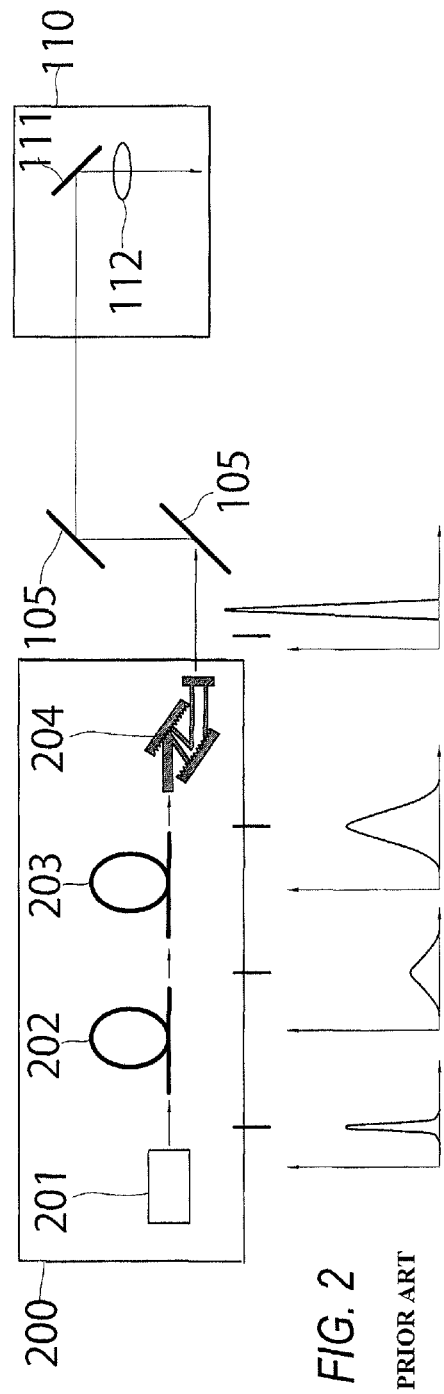
FIG. 1 PRIOR ART
FIG. 2 PRIOR ART

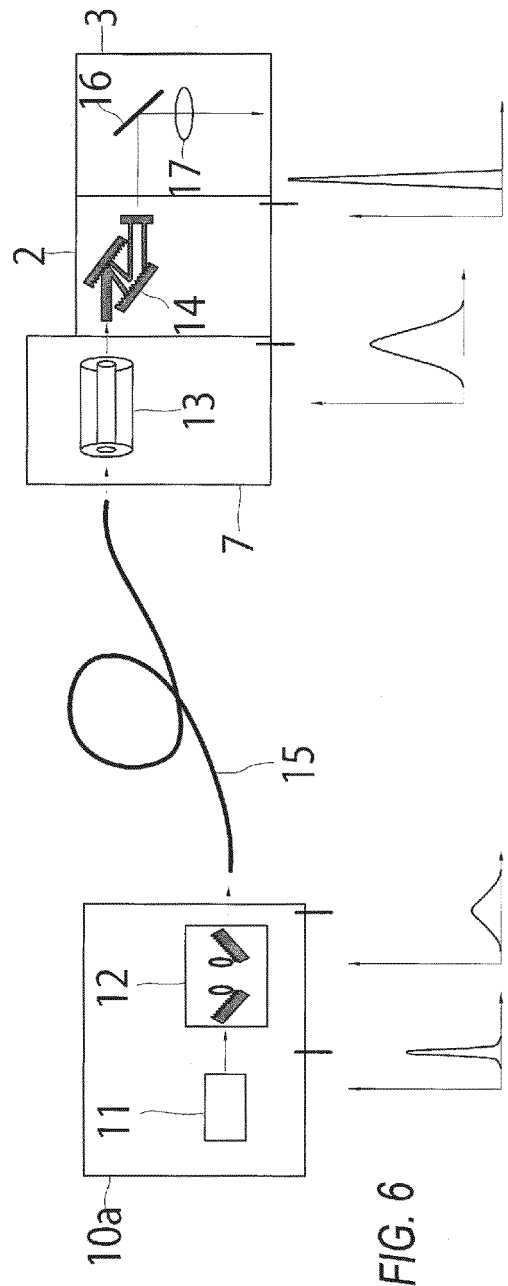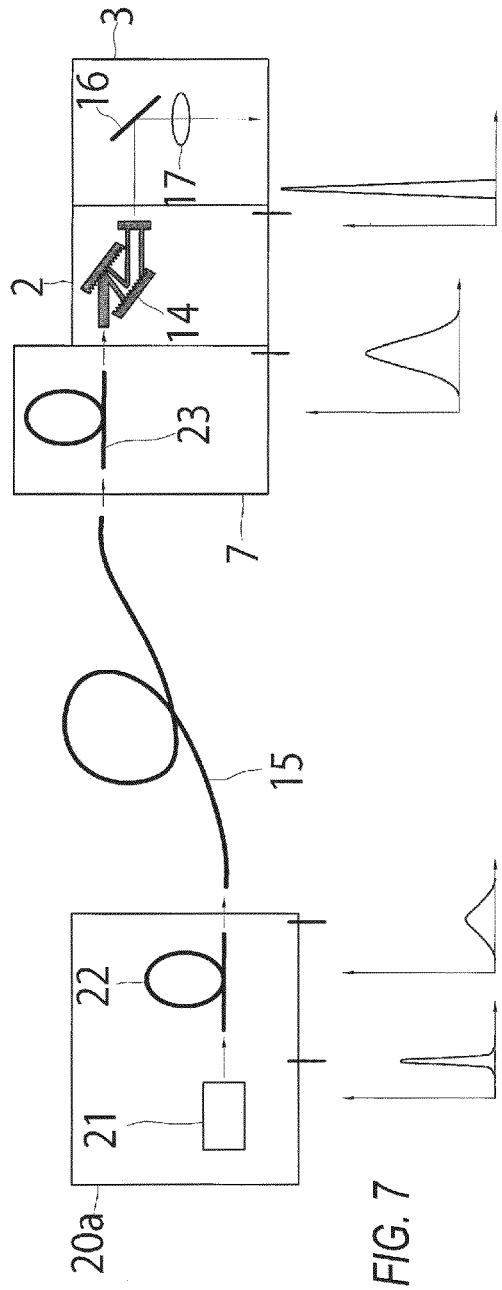

ULTRASHORT PULSE LASER PROCESSING APPARATUS

BACKGROUND

The present invention relates to an ultrashort pulse laser processing apparatus for processing a processing target such as a tissue of a processing target's eye.

Apparatuses are suggested which are able to perform micro processing of the processing target by emitting an ultrashort pulse laser beam such as a femtosecond laser beam (see UEHARA, Yuzuru et al. "Micro processing fiber laser" Laser processing academic journal Vol. 14, No. 3 (2007) p. 159 to 163). Since the pulse laser beam does not involve heating, also does not require selection of the target material, is able to perform the micro processing of a micron order, and is able to perform internal processing of a transparent target, the pulse laser beam has received much attention in recent years.

SUMMARY

Herein, a laser processing apparatus of the related art capable of outputting the femtosecond laser beam will be described. FIG. 1 is a schematic configuration diagram of a laser processing apparatus of the related art using a laser head of a solid element type. FIG. 2 is a schematic configuration diagram of a laser processing apparatus of the related art using a laser head of an optical fiber type.

In the case of the apparatus of FIG. 1, a laser head 100 includes a femtosecond pulse seed optical laser 101, a diffraction grating stretcher 102, a solid amplifier 103, and a diffraction grating compressor 104. The laser beam, which is output from the laser head 100, is guided by an optical transmission system 105 due to a total reflection mirror, and is emitted to the target by an emission end unit 110 including a scanner 111 and a condensing lens 112. A lower part of FIG. 1 shows a state of the laser beam (the laser pulse) at this time. In the graph showing a state of the laser beam, a transverse axis is time, and a longitudinal axis is energy intensity. The laser beam (the laser pulse) from the laser 101 is stretched by the stretcher 102, is amplified by the solid amplifier 103 and is compressed by the compressor 104 such that a peak power thereof exceeds 1 kilowatt.

Furthermore, in the case of the apparatus of FIG. 2, the laser head 200 includes a femtosecond pulse seed optical laser 201, a fiber stretcher 202, a fiber amplifier 203, and a diffraction grating compressor 204. The laser beam, which is output from the laser head 200, is guided by the optical transmission system 105 due to the total reflection mirror, and is emitted to the target by the emission end unit 110 including the scanner 111 and the condensing lens 112. A lower part of FIG. 2 shows a state of the laser beam at this time. In the graph showing a state of the laser beam, a transverse axis thereof is the time, and a longitudinal axis thereof is the energy intensity. The laser beam from the laser 201 is stretched by the stretcher 202, is amplified by the solid amplifiers 103 and 203, and is compressed by the compressor 204 such that a peak power thereof exceeds 1 kilowatt.

In the apparatuses of FIGS. 1 and 2, the compressed laser beam is guided by the optical transmission system 105 and is sent to the emission end unit 110. However, a unit receiving the optical transmission system 105, for example, an arm or the like is inferior in operability, and the flexible handling of the emission end unit 110 is difficult.

An object of the present invention is to provide an ultrashort pulse laser processing apparatus which enables the flexible handling of the emission end unit of the laser beam.

The present invention was configured as below in order to solve the problem mentioned above.

(1) An ultrashort pulse laser processing apparatus for processing a processing target, comprising:

a laser head configured to emit a laser pulse, the laser head including a seed laser-source configured to emit an ultrashort pulse seed laser;

an optical fiber configured to guide the laser pulse emitted from the laser head; and an emission end unit which includes a compressor configured to compress the laser pulse emitted from the optical fiber to a laser pulse of a predetermined high peak power and emits the laser pulse compressed by the compressor to the target.

(2) The ultrashort pulse laser processing apparatus according to (1), wherein the optical fiber includes a fiber amplifier configured to amplify the laser pulse, and the laser head includes an stretcher which stretches the seed laser emitted from the seed laser source.

(3) The ultrashort pulse laser processing apparatus according to (1), wherein the optical fiber includes a fiber stretcher configured to stretch the laser pulse, and the emission end unit includes an amplifier configured to amplify the laser pulse stretched with the fiber stretcher.

(4) The ultrashort pulse laser processing apparatus according to (1) further comprising:

a fiber stretcher configured to stretch the seed laser emitted from the seed laser source; and a fiber amplifier configured to amplify the laser fiber stretched by the fiber stretcher, wherein the optical fiber is a fiber of the fiber stretcher or a fiber of the fiber amplifier.

According to the present invention, it is possible to perform the flexible handling of the emission end unit of the laser beam.

BRIEF DESCRIPTION OF THE DRAWINGS

FIG. 1 shows a schematic configuration of a laser processing apparatus of the related art using a laser head of a solid element type, and a diagram that shows a state of the laser beam.

FIG. 2 shows a schematic configuration of a laser processing apparatus of the related art using a laser head of an optical fiber type, and a diagram that shows a state of the laser beam.

FIG. 6 is a diagram that shows the laser head of the solid element type received in the main body portion, the amplification portion, the compression portion, the emission end unit, and the optical fiber connecting the laser head with the compression portion and a diagram that shows a state of the laser beam.

FIG. 7 is a diagram that shows the laser head of the optical fiber type received in the main body portion, the amplification portion, the compression portion, the emission end unit, and the optical fiber connecting the laser head with the compression portion and a diagram that shows a state of the laser beam.

DESCRIPTION OF EXEMPLARY EMBODIMENTS

Figure 3:
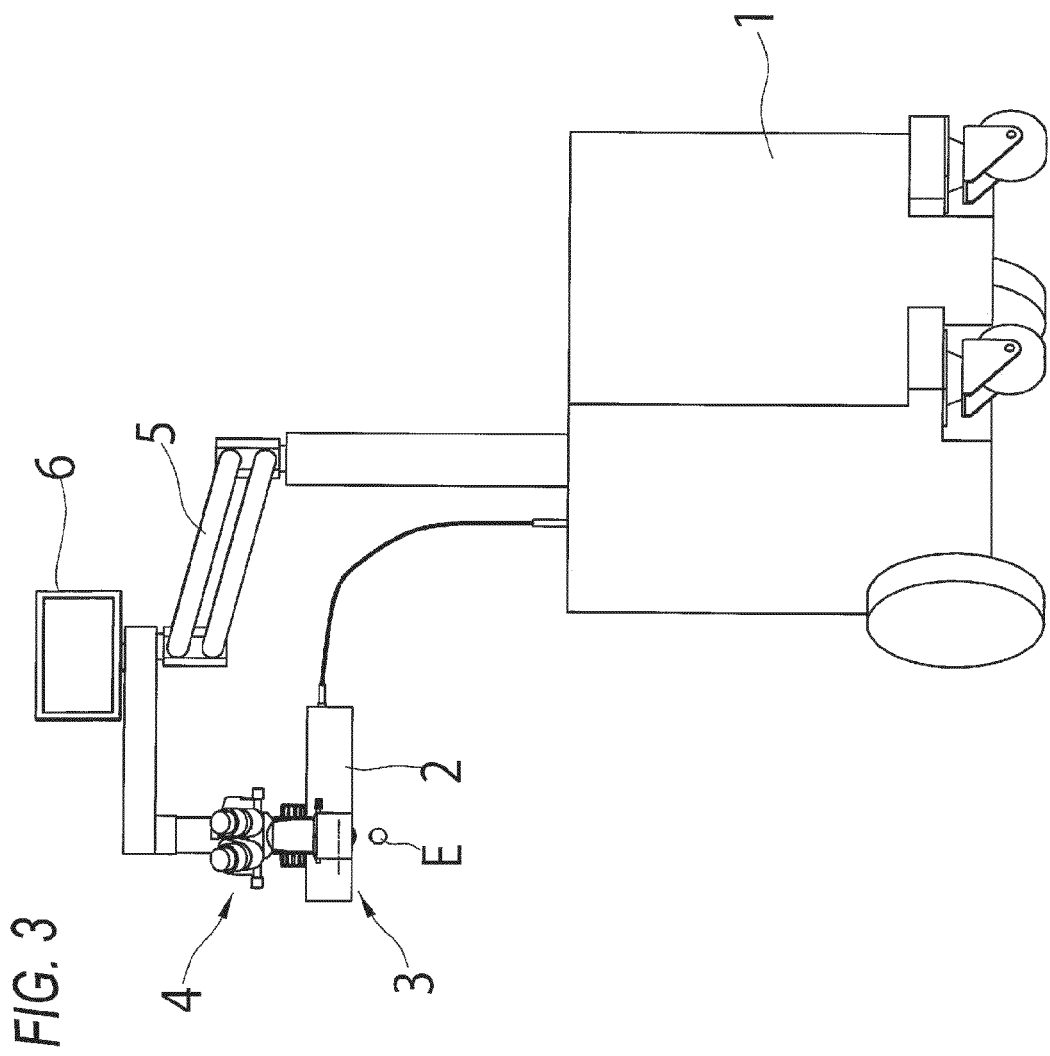
FIG. 3 is a schematic configuration diagram of an ultrashort pulse laser processing apparatus that is an embodiment of the present invention.

Hereinafter, an exemplary embodiment will be described with reference to the drawings. FIG. 3 is a schematic configuration diagram (an outside view) of an ultrashort pulse laser processing apparatus in an embodiment of the present invention. In addition, the laser processing apparatus of the present embodiment is an apparatus for processing a tissue (a cornea, a crystalline lens or the like) of a processing target's eye (a patient's eye) that is a processing target.

A laser head 10 or 20 or the like described later are received in a main body portion 1 of the laser processing apparatus. The laser beam output from the laser head 10 or 20 is sent to a compression portion 2 by an optical fiber (an optical guiding fiber) 15. The laser beam compressed by a compressor 14 described later in a compression portion 2 is sent to an emission end unit 3 that is connected to the compression portion 2. A scanner 16 and a condensing lens 17 described later are received in the emission end unit 3, and the laser beam transmitted to the emission end unit 3 is emitted while being scanned to a desired site of a processing target eye E.

In addition, the emission end unit 3 is provided with a microscope portion 4 of both eyes for observing the eye E by an operator of the apparatus (a technician in the present embodiment).

The emission end unit 3 is connected to the main body portion 1 by an articulated arm 5 (that is, the emission end unit 3 is suspended and supported by the main body portion 1 and the arm 5). Since the arm 5 does not guide the laser beam (does not receive the optical transmission system due to the total reflection mirror), the arm 5 can have many joint portions. As a consequence, it is possible to flexibly handle the emission end unit 3 provided at the tip of the arm 5 (the operability of the arm 5 is excellent).

Furthermore, a touch panel type display 6 is attached to the arm 5. The display 6 enables the setting of various irradiation parameters of the laser beam which are the processing conditions (surgical conditions), and is able to display 6 the set conditions (the parameters) or the like.

Figure 4:
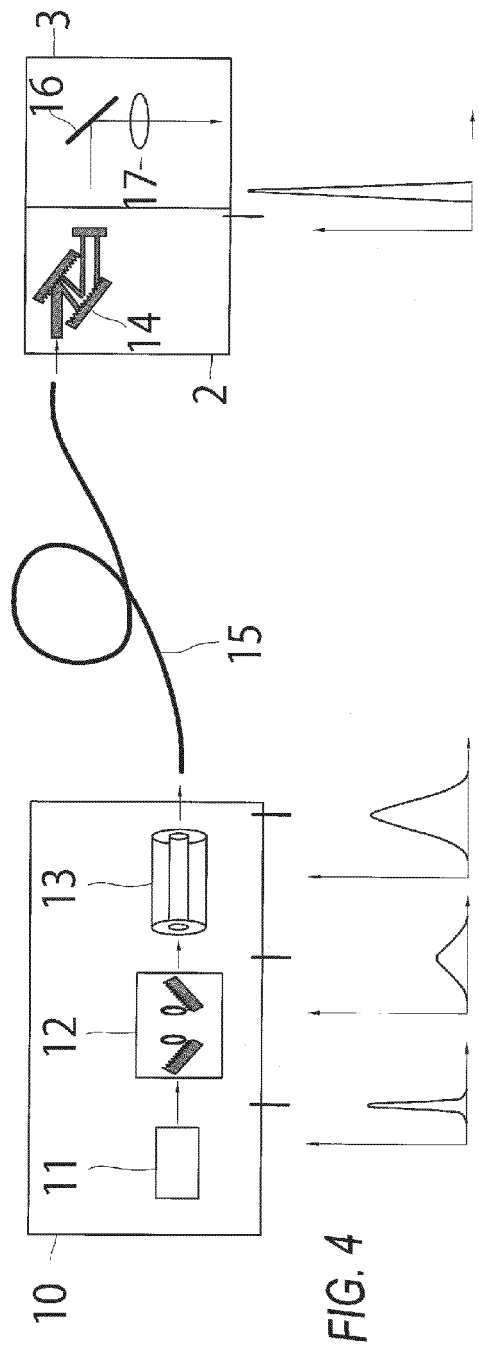
FIG. 4 is a diagram that shows the laser head of the solid element type received in a main body portion, the compression portion, the emission end unit, and the optical fiber connecting the laser head with the compression portion and shows a state of the laser beam.

FIG. 4 shows the laser head 10 of the solid element type received in the main body portion 1, the compression portion 2, the optical emission portion 3, and the optical fiber 15. In addition, the optical fiber 15 sends the laser beam from the laser head 20 to the compressor 14 in the compression portion 2.

The laser head 10 includes the femtosecond pulse seed optical laser 11, the diffraction grating stretcher 12, and solid amplifier 13. The laser beam, which is output from the laser head 10, is guided by the optical fiber 15, is compressed by the diffraction grating compressor 14 in the compression portion 2, and is emitted to the eye E by the emission end unit 3 including the scanner 16 and the condensing lens 17. A lower part of FIG. 4 shows the state of the laser beam at this time. In the graph showing the state of the laser beam, a transverse axis is the time, and a longitudinal axis is the energy intensity. The laser beam from the laser 11 is stretched by the stretcher 12, is amplified by the amplifier 13, and is compressed by the compressor 14 so that the peak power thereof exceeds 1 kilowatt.

Figure 5:
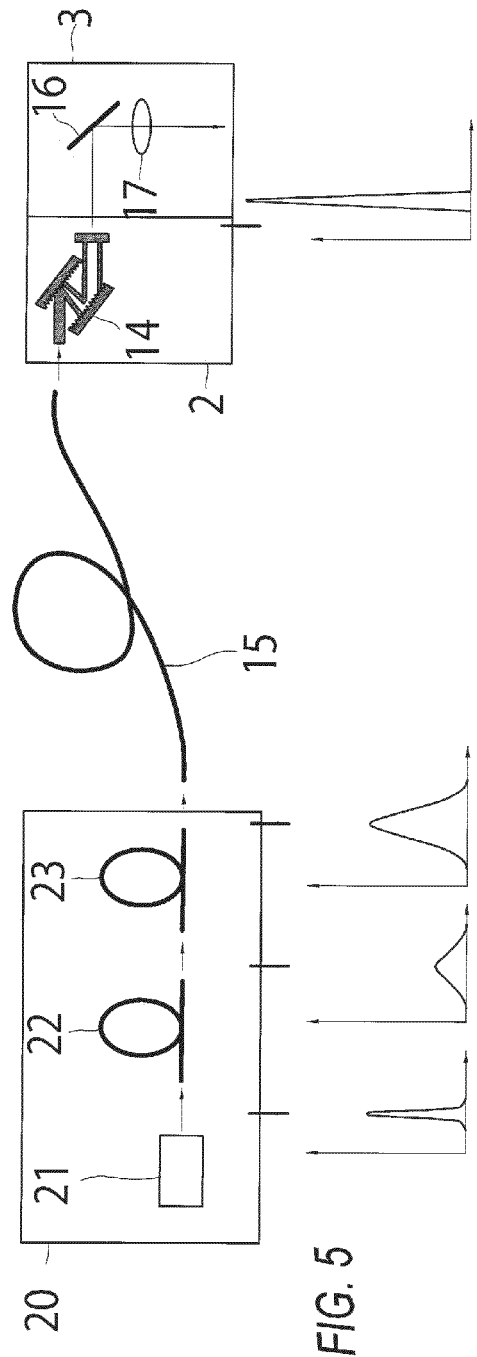
FIG. 5 is a diagram that shows the laser head of the optical fiber type received in the main body portion, the compression portion, the emission end unit, and the optical fiber connecting the laser head with the compression portion and shows a state of the laser beam.

FIG. 5 shows the laser head 20 of the optical fiber type received in the main body portion 1, the compression portion 2, the ejection end unit 3, and the optical fiber 15 which connects the laser head 20 and the compressor 14 in the compression portion 2. In addition, the optical fiber 15 sends the laser beam from the laser head 20 to the compressor 14 in the compression portion 2.

The laser head 20 includes the femtosecond pulse seed optical laser 21, the fiber stretcher 22, and the fiber amplifier 23. The laser beam output from the laser head 20 is guided by the optical fiber 15, is compressed by the diffraction grating compressor 14 in the compression portion 2, and is emitted to the eye E by the emission end unit 3 including the scanner 16 and the condensing lens 17. A lower part of FIG. 5 shows the state of the laser beam at this time. In the graph showing the state of the laser beam, a transverse axis is the time, and a longitudinal axis is the energy intensity. The laser beam from the laser 21 is stretched by the stretcher 22, is amplified by the amplifier 23, and is compressed by the compressor 24 so that the peak power thereof exceeds 1 kilowatt.

Like the example of the related art (the apparatuses of FIGS. 1 and 2), when the amplifier and the compressor are directly connected to each other, the laser beam compressed so that the peak power thereof exceeds 1 kilowatt needs to be reliably sent to the emission end unit, it is difficult to use the optical fiber as the optical guiding means, and thus the optical transmission system by the total reflection mirror is used. Accordingly, the laser beam is pinned by the optical transmission system by the total reflection mirror. In this case, since the handling of the emission end unit may be reduced, the articulated arm can be used (the arm receives the optical transmission system by the mirror). However, since the optical axis adjustment of the mirror or the like greatly varies, it is impossible to provide many articulation portions. As a consequence, it is difficult to perform the flexible handling of the emission end unit.

On the contrary to the example described above, like the embodiment of the present invention (the apparatuses of FIGS. 4 and 5), by connecting the compression portion received in the compressor to the emission end unit and connecting the amplifier and the compressor by the optical fiber, the flexible handling of the emission end unit becomes possible. Moreover, as shown in FIGS. 4 and 5, the setting is performed so that the peak power of the laser beam stretched by the stretcher and amplified by the amplifier does not exceed 1 kilowatt and the peak power of the laser beam guided by the optical fiber and compressed by the compressor exceeds 1 kilowatt. As a result, it is possible to send the laser beam stretched by the stretcher and amplified by the amplifier to the compressor via the optical fiber.

In addition, it is preferable that the optical fiber used in the embodiment of the present invention be ideally a single-mode fiber having a small numerical aperture (NA) and having a core diameter greater than 30 μm. However, when the numerical aperture (NA) is too small, the guide characteristics as the waveguide is weak, and it is impossible to bend the optical fiber, which ruins miniaturization, lightweight, operability or the like which are advantages of using the optical fiber as the optical guiding means.

Next, another embodiment (a modified example) of the present invention will be described based on the drawings.

FIG. 6 shows a laser head 10a of a solid element type received in the main body portion 1, an amplification portion 7 (not shown) connected to the compression portion 2, the compression portion 2, the emission end unit 3, and the optical fiber 15 which connects (sends the laser beam from the laser head 10a to the amplifier 13 or 23 in the amplification portion 7) the laser head 10a with the amplifier 13 or 23 in the amplification portion 7.

As shown in FIG. 6, the laser head 10a includes a femtosecond pulse seed optical laser 11 and a diffraction grating stretcher 12. The laser beam output from the laser head 10a is guided by the optical fiber 15, is amplified by the solid amplifier 13 in the amplification portion 7, is compressed by the diffraction grating amplifier 14 in the compression portion 2, and is emitted to the eye E by the emission end unit 3 including the scanner 16 and the condensing lens 17. A lower part of FIG. 6 shows the state of the laser beam at this time. In the graph showing the state of the laser beam a transverse axis is the time, and a longitudinal axis is the energy intensity. As shown in FIG. 6, the laser beam from the laser 11 is stretched by the stretcher 12, is amplified by the amplifier 13, and is compressed by the compressor 14 so that the peak power thereof exceeds 1 kilowatt.

FIG. 7 shows a laser head 20a of an optical fiber type received in the main body portion 1, an amplifier (not shown) 7 connected to the compression portion 2, the compression portion 2, the ejection end unit 3, and the optical fiber 15 which connects (sends the laser beam from the laser head 20 to the amplifier 13 or 23 in the amplifier portion 7) the laser head 20a with the amplifier 13 or 23 in the amplification portion 7.

The laser head 20a includes the femtosecond pulse seed optical laser 21, and the fiber stretcher 22. The laser beam output from the laser head 20a is guided by the optical fiber 15, is amplified by the fiber amplifier 23 in the amplification portion 7, is compressed by the diffraction grating compressor 14 in the compression portion 2, and is emitted to the eye E by the emission end unit 3 including the scanner 16 and the condensing lens 17. A lower part of FIG. 7 shows the state of the laser beam at this time. In the graph showing the state of the laser beam, a transverse axis is the time, and a longitudinal axis is the energy intensity. The laser beam from the laser 21 is stretched by the stretcher 22, is amplified by the amplifier 23, and is compressed by the compressor 24 so that the peak power thereof exceeds 1 kilowatt.

Like another embodiment of the present invention (the apparatuses of FIGS. 6 and 7), by connecting the amplification portion with the amplifier received therein and the compression portion with the compressor received therein to the emission end unit and connecting the stretcher with the amplifier by the optical fiber, the flexible handling of the emission end unit becomes possible. Moreover, as shown in FIGS. 6 and 7, the setting is performed so that the peak power of the laser beam stretched by the stretcher does not exceed 1 kilowatt and the peak power of the laser beam guided by the optical fiber exceeds 1 kilowatt. As a result, it is possible to send the laser beam stretched by the stretcher and amplified by the amplifier to the amplifier via the optical fiber.

Furthermore, since the apparatus using the optical fiber type laser head is able to directly connect the fiber stretcher, the fiber amplifier, the optical guiding fiber as one bundle of fibers, the apparatus has high stability, the optical axis adjustment is also easy, and is advantageous compared to an apparatus using the laser head of the solid element type. Furthermore, the fiber amplifier and the optical guiding fiber can have the same fiber configuration, which is more advantageous in the stability or the like.

In addition, in the embodiments mentioned above, the femtosecond pulse seed optical laser has been used as the seed optical laser source, but the present invention is not limited thereto. The seed optical laser may be adopted which generates the laser beam of the ultrashort pulse such as the picoseconds pulse having the characteristics which does not involve the heating, the material of the target is not also selected, allows the minute processing of the micron order, and allows the internal processing of the transparent target or the like.

Furthermore, in the embodiment mentioned above, the optical guiding fiber and the compressor in the compression portion or the amplifier in the amplification portion are directly connected to each other, but the connection may be performed by a connector (not shown), and the optical guiding fiber may be detachable from the compressor or the amplifier. Moreover, the detached optical guiding fiber may be connected and used to the compressor in the compression portion or the amplifier in the amplification portion connected to the emission end unit of another apparatus.

Furthermore, in the embodiment mentioned above, the connection portion is connected to the emission end unit, but the connection may be performed via a connector (not shown), and the compression portion may be detachable from the emission end unit. Moreover, the detached compression portion may be connected and used to the emission end unit of another apparatus.

In addition, in the embodiment mentioned above, the diffraction grating compressor using the diffraction grating is used as the compressor, but the invention is not limited thereto. A configuration in which the pulse laser can be compressed, that is the laser pulse is compressed with high peak may be applied. For example, a configuration in which a prism or a chirp mirror is used.

What is claimed is:

1. An ultrashort pulse laser processing apparatus for processing a tissue of a patient's eye that is a processing target, comprising:
    a main body portion;
    a laser head configured to emit a laser pulse, the laser head including a seed laser source configured to emit an ultrashort pulse seed laser and a stretcher configured to stretch the seed laser emitted by the seed laser source, the laser head being arranged at the main body portion;
    an emission end unit which includes a compressor configured to compress the laser pulse emitted from the laser head to an ultrashort pulse laser beam having a high peak power, the emission end unit being separated from the main body portion and to illuminate the tissue of the patient's eye with the ultrashort pulse laser beam;
    an optical fiber configured to guide the laser pulse emitted from the laser head to the emission end; and
    an arm configured to movably support the emission end with respect to the main body portion,
    wherein:
    the optical fiber is detachably connected to the main body portion via a connector and detachably connected to the emission end unit; and
    the arm does not guide the laser beam.

2. The ultrashort pulse laser processing apparatus according to claim 1, wherein
    the optical fiber includes a fiber amplifier for amplifying the laser pulse stretched by the stretcher.

3. The ultrashort pulse laser processing apparatus according to claim 1, wherein
    the emission end unit includes an amplifier configured to amplify the laser pulse guided by optical fiber.

4. The ultrashort pulse laser processing apparatus according to claim 1, wherein
    the optical fiber includes at least one of:
    a fiber stretcher configured as the stretcher; and
    a fiber amplifier configured to amplify the laser fiber stretched by the fiber stretcher.

5. The ultrashort pulse laser processing apparatus according to claim 1, wherein
the emission end unit includes an amplifier configured to amplify the laser pulse, the amplifier being connected to the compressor; and
the optical fiber is detachably connected to the stretcher via a connector and detachably connected to the amplifier via a connecter.

* * * * *